(12) United States Patent
McInally et al.

(10) Patent No.: US 8,673,907 B2
(45) Date of Patent: Mar. 18, 2014

(54) PHARMACEUTICALLY ACCEPTABLE SALTS OF METHYL (3-{ [[3-(6-AMINO-2-BUTOXY-8-OXO-7,8-DIHYDRO-9H-PURIN-9-YL) PROPYL] (3-MORPHOLIN-4-YLPROPYL) AMINO] METHYL }PHENYL) ACETATE AND THEIR USE IN THERAPY

(75) Inventors: Thomas McInally, Leicestershire (GB); Håkan Schulz, Lund (SE)

(73) Assignees: AstraZeneca AB, Södertälje (SE); Dainippon Sumitomo Pharma Co., Ltd., Osaka (JP)

( * ) Notice: Subject to any disclaimer, the term of this patent is extended or adjusted under 35 U.S.C. 154(b) by 0 days.

(21) Appl. No.: 12/808,627

(22) PCT Filed: Dec. 16, 2008

(86) PCT No.: PCT/SE2008/051465
§ 371 (c)(1),
(2), (4) Date: Aug. 10, 2011

(87) PCT Pub. No.: WO2009/078798
PCT Pub. Date: Jun. 25, 2009

(65) Prior Publication Data
US 2011/0294802 A1 Dec. 1, 2011

Related U.S. Application Data

(60) Provisional application No. 61/014,164, filed on Dec. 17, 2007.

(51) Int. Cl.
*A61K 31/535* (2006.01)
*C07D 413/00* (2006.01)

(52) U.S. Cl.
USPC ........................... 514/234.2; 544/118

(58) Field of Classification Search
USPC ....................... 544/118; 514/234.2
See application file for complete search history.

(56) References Cited

U.S. PATENT DOCUMENTS

| | | | |
|---|---|---|---|
| 3,832,460 A * | 8/1974 | Kosti | 424/54 |
| 4,179,562 A | 12/1979 | Ponsford et al. | |
| 4,572,909 A * | 2/1986 | Campbell et al. | 514/356 |
| 4,619,936 A * | 10/1986 | Balkanyi et al. | 514/282 |
| 4,689,338 A | 8/1987 | Gerster | |
| 4,698,348 A | 10/1987 | Gerster | |
| 4,714,701 A | 12/1987 | Beauchamp | |
| 4,912,112 A | 3/1990 | Seydel et al. | |
| 5,543,407 A * | 8/1996 | Guodong | 514/226.2 |
| 5,614,178 A * | 3/1997 | Bloom et al. | 424/60 |
| 5,736,549 A | 4/1998 | Beasley et al. | |
| 5,763,476 A * | 6/1998 | Delbressine et al. | 514/410 |
| 5,795,909 A * | 8/1998 | Shashoua et al. | 514/449 |
| 5,994,361 A | 11/1999 | Penney et al. | |
| 6,028,076 A | 2/2000 | Hirota et al. | |
| 6,110,923 A | 8/2000 | Ely | |
| 6,132,286 A * | 10/2000 | Murthy et al. | 446/318 |
| 6,329,381 B1 | 12/2001 | Kurimoto et al. | |
| 6,358,527 B1 * | 3/2002 | Gilis et al. | 424/474 |
| 6,376,501 B1 | 4/2002 | Isobe et al. | |
| 6,448,236 B1 | 9/2002 | Monaghan et al. | |
| 6,458,798 B1 | 10/2002 | Fujita et al. | |
| 6,608,101 B1 * | 8/2003 | NI et al. | 514/443 |
| 6,624,138 B1 * | 9/2003 | Sung et al. | 514/1 |
| 6,630,478 B2 | 10/2003 | Diamond et al. | |
| 6,887,880 B2 | 5/2005 | Levy et al. | |
| 6,951,866 B2 | 10/2005 | Fujita et al. | |
| 7,157,465 B2 | 1/2007 | Isobe et al. | |
| 7,167,750 B2 * | 1/2007 | Knudson et al. | 607/40 |
| 7,442,806 B2 * | 10/2008 | Merli et al. | 548/525 |
| 7,521,454 B2 | 4/2009 | Isobe et al. | |
| 7,642,350 B2 | 1/2010 | Pryde | |
| 7,645,802 B2 * | 1/2010 | Oberegger et al. | 514/649 |
| 7,649,010 B2 * | 1/2010 | Chen et al. | 514/411 |
| 7,667,069 B2 * | 2/2010 | Pinza et al. | 560/250 |
| 7,691,877 B2 | 4/2010 | Jones et al. | |
| 7,754,728 B2 | 7/2010 | Isobe et al. | |
| 8,012,964 B2 * | 9/2011 | Kurimoto et al. | 514/234.2 |
| 2002/0040032 A1 | 4/2002 | Glasky et al. | |
| 2002/0128264 A1 | 9/2002 | Taylor et al. | |
| 2003/0144283 A1 | 7/2003 | Coleman et al. | |

(Continued)

FOREIGN PATENT DOCUMENTS

| | | |
|---|---|---|
| CA | 1220148 | 4/1987 |
| CN | 101239980 | 8/2008 |

(Continued)

OTHER PUBLICATIONS

"Chronic obstructive pulmonary disease"(AllRefer.com Health) <http://health.allrefer.com/health/chronic-obstructive-pulmonary-disease-prevention.html> downloaded from the internet Jun. 24, 2010.
"Respiratory experts call for global approach to treat chronic diseases" Feb. 13, 2007 <http://www.medwire-news.md/48/64443/Respiratory/Respiratory_experts_call_for_global_approach_to_treat_chronic_disease.html> downloaded from the internet Jun. 24, 2010.
"Asthma" (MDAdvice.com) < http://www.mdadvice.com/topics/asthma/info/1.htm> downloaded from the internet Jun. 24, 2010.
Aoki et al., "Weekly dosing of AZD8848/DSP-3025, a novel TLR7 agonist antedrug, demonstrates a prolonged period of control against markers of pulmonary inflammation in an alergen challenge model in the mouse," ATS, New Orleans, May 2010.
Bell et al., "AZD8848/Dsp-3025, a novel potent TLR7 agonist antedrug, demonstrates negligible systemic activity and a prolonged period of control after cessation of weekly dosing in a brown Norway rat ovalbumin challenge model," ATS, New Orleans, May 2010.
Biffen et al., "Biological activity of a novel TLR7 agaonist antedrug for the treatment of allergic diseases," ATS, New Orleans, May 2010.
Chavarot, "Synthesis of an adenine-pyridinaldoxime-acridine conjugate for recognition of abasic site lesions in DNA," Tetrahedron, 1997, 53(40), pp. 13749-13756.
Drazen "Surgery for Emphysema—Not for Everyone" N. Engl. J. Med. 345(15): 1126-1128 (2001).

(Continued)

*Primary Examiner* — Noble Jarrell
*Assistant Examiner* — Laura Daniel
(74) *Attorney, Agent, or Firm* — Morgan, Lewis & Bockius LLP

(57) ABSTRACT

The present invention concerns hydrochloric acid, hydrobromic acid and maleic acid salts of methyl (3-{[[3-(6-amino-2-butoxy-8-oxo-7,8-dihydro-9H-purin-9-yl)propyl](3-morpholin-4-ylpropyl)amino]methyl}phenyl)acetate, compositions comprising them and their use in therapy.

7 Claims, 3 Drawing Sheets

(56) References Cited

U.S. PATENT DOCUMENTS

| | | |
|---|---|---|
| 2003/0191086 A1 | 10/2003 | Hanus et al. |
| 2003/0212092 A1 | 11/2003 | Heppner et al. |
| 2004/0019048 A1 | 1/2004 | Crooks et al. |
| 2004/0204438 A1 | 10/2004 | Crooks et al. |
| 2004/0214192 A1 | 10/2004 | Hashida et al. |
| 2004/0229897 A1 | 11/2004 | Crooks et al. |
| 2004/0254385 A1* | 12/2004 | Sathyanarayana et al. ... 549/467 |
| 2005/0054590 A1 | 3/2005 | Averett |
| 2005/0119273 A1 | 6/2005 | Lipford et al. |
| 2006/0052403 A1 | 3/2006 | Isobe et al. |
| 2006/0223794 A1* | 10/2006 | Bourghol Hickey et al. . 514/220 |
| 2006/0252774 A1 | 11/2006 | Vatner et al. |
| 2007/0088049 A1* | 4/2007 | Lorimer et al. ............... 514/301 |
| 2007/0112039 A1* | 5/2007 | Grant et al. .................... 514/352 |
| 2007/0142451 A1* | 6/2007 | Chen et al. .................... 514/411 |
| 2007/0190071 A1 | 8/2007 | Kurimoto et al. |
| 2007/0225303 A1 | 9/2007 | Ogita et al. |
| 2007/0249638 A1 | 10/2007 | Giorgio et al. |
| 2008/0008682 A1 | 1/2008 | Chong et al. |
| 2008/0176905 A1* | 7/2008 | Ini et al. ........................ 514/342 |
| 2008/0269240 A1 | 10/2008 | Hashimoto et al. |
| 2008/0287519 A1* | 11/2008 | Mendelovici et al. ........ 514/414 |
| 2008/0300244 A1 | 12/2008 | Bonnert et al. |
| 2009/0047249 A1 | 2/2009 | Graupe et al. |
| 2009/0082332 A1 | 3/2009 | Abbot et al. |
| 2009/0099216 A1 | 4/2009 | Millichip et al. |
| 2009/0105212 A1 | 4/2009 | Isobe et al. |
| 2009/0118263 A1 | 5/2009 | Hashimoto et al. |
| 2009/0131458 A1 | 5/2009 | Lazarides et al. |
| 2009/0143400 A1 | 6/2009 | McInally et al. |
| 2009/0192153 A1 | 7/2009 | Hashimoto et al. |
| 2009/0202484 A1 | 8/2009 | Chong et al. |
| 2009/0209524 A1 | 8/2009 | Bennett et al. |
| 2009/0281075 A1 | 11/2009 | Roughton et al. |
| 2009/0324551 A1 | 12/2009 | Carson et al. |
| 2009/0325877 A1 | 12/2009 | Grunt et al. |
| 2010/0041687 A1* | 2/2010 | Thon ............................ 514/275 |
| 2010/0075995 A1 | 3/2010 | Biggadike et al. |
| 2010/0081668 A1* | 4/2010 | Neu et al. ................. 514/254.04 |
| 2010/0087443 A1 | 4/2010 | Bonnert et al. |
| 2010/0093998 A1 | 4/2010 | Isobe et al. |
| 2010/0099870 A1 | 4/2010 | Isobe et al. |
| 2010/0120799 A1 | 5/2010 | Lazarides et al. |
| 2010/0130491 A1 | 5/2010 | Bonnert et al. |
| 2010/0168245 A1* | 7/2010 | Wainer et al. ................. 514/653 |
| 2010/0240623 A1 | 9/2010 | Cook et al. |
| 2010/0256118 A1 | 10/2010 | Isobe et al. |
| 2010/0280001 A1 | 11/2010 | Bonnert et al. |
| 2010/0298364 A1 | 11/2010 | Bennett et al. |
| 2011/0028715 A1 | 2/2011 | Isobe et al. |
| 2011/0046369 A1* | 2/2011 | Hashimoto et al. ............ 544/118 |
| 2011/0054168 A1* | 3/2011 | Kurimoto et al. ............. 544/118 |
| 2011/0136801 A1 | 6/2011 | Isobe et al. |
| 2011/0306610 A1* | 12/2011 | Kurimoto et al. .......... 514/234.2 |

FOREIGN PATENT DOCUMENTS

| | | |
|---|---|---|
| EP | 1035123 | 8/2003 |
| EP | 1550662 | 7/2005 |
| EP | 1728793 | 12/2006 |
| EP | 1908480 | 4/2008 |
| EP | 2246353 | 11/2010 |
| GB | 1375162 | 11/1974 |
| JP | 08-165292 | 6/1996 |
| JP | 347422/1997 | 11/1997 |
| JP | 367449/1997 | 12/1997 |
| JP | 367451/1997 | 12/1997 |
| JP | 10-501533 | 2/1998 |
| JP | 11-180981 | 7/1999 |
| JP | 11-180982 | 7/1999 |
| JP | 11-193282 | 7/1999 |
| JP | 2000-159767 | 6/2000 |
| JP | 2004-137157 | 5/2004 |
| JP | 2005-089334 | 4/2005 |
| WO | WO 95/35297 | 12/1995 |
| WO | WO 96/11200 | 4/1996 |
| WO | WO 98/01448 | 1/1998 |
| WO | WO 99/28321 | 6/1999 |
| WO | WO 99/32122 | 7/1999 |
| WO | WO 00/12487 | 3/2000 |
| WO | WO 00/43394 | 7/2000 |
| WO | WO 00/76519 | 12/2000 |
| WO | WO 01/27131 | 4/2001 |
| WO | WO 02/04449 | 1/2002 |
| WO | WO 02/04451 | 1/2002 |
| WO | WO 02/40481 | 5/2002 |
| WO | WO 02/85905 | 10/2002 |
| WO | WO 03/011864 | 2/2003 |
| WO | WO 2004/011481 | 2/2004 |
| WO | WO 2004/029054 | 4/2004 |
| WO | WO 2004/075865 | 9/2004 |
| WO | WO 2004/087049 | 10/2004 |
| WO | WO 2005/025583 | 3/2005 |
| WO | WO 2005/092892 | 10/2005 |
| WO | WO 2005/092893 | 10/2005 |
| WO | WO 2006/029115 | 3/2006 |
| WO | WO 2006/091394 | 8/2006 |
| WO | WO 2006/117670 | 11/2006 |
| WO | WO 2006/129784 | 12/2006 |
| WO | WO 2007/024707 | 3/2007 |
| WO | WO 2007/031726 | 3/2007 |
| WO | WO 2007/034173 | 3/2007 |
| WO | WO 2007/034817 | 3/2007 |
| WO | WO 2007/034881 | 3/2007 |
| WO | WO 2007/034882 | 3/2007 |
| WO | WO 2007/034916 | 3/2007 |
| WO | WO 2007/034917 | 3/2007 |
| WO | WO 2007/093901 | 8/2007 |
| WO | WO 2008/004948 | 1/2008 |
| WO | WO 2008/005555 | 1/2008 |
| WO | WO 2008/071976 | 6/2008 |
| WO | WO 2008/101867 | 8/2008 |
| WO | WO 2008/114006 | 9/2008 |
| WO | WO 2008/114008 | 9/2008 |
| WO | WO 2008/114817 | 9/2008 |
| WO | WO 2008/114819 | 9/2008 |
| WO | WO 2008/135791 | 11/2008 |
| WO | WO 2009/005687 | 1/2009 |
| WO | WO 2009/062059 | 5/2009 |
| WO | WO 2009/067081 | 5/2009 |
| WO | WO 2009/078798 | 6/2009 |
| WO | WO 2009/091031 | 7/2009 |
| WO | WO 2009/091032 | 7/2009 |
| WO | WO 2010/033074 | 3/2010 |
| WO | WO 2010/133882 | 11/2010 |

OTHER PUBLICATIONS

Dvorakova, "Synthesis of 2'-aminomethyl derivatives of N-(2-(phosphonomethoxy)ethyl) nucleotide analogues as potential antiviral agents," J. Med. Chem., 1996, 39(17), pp. 3263-3268.

Fridkin "Vancomycin-intermediate and -resistant *Staphylococcus aureus*: what the infectious disease specialist needs to know" Clinical Infectious Diseases 32(1):108-115 (2001).

Hirota et al., "Discovery of 8-hydroxyadenines as a novel type of interferon inducer," J. Med. Chem., 2002, 45 (25), pp. 5419-5422.

Holy et al., "Studies on S-adenosyl-L-homocysteine hydrolase. XVI. 9-(Aminoalkyl)-8-hydroxyadenines: preparation mechanism of formation, and use in affinity chromatography of S-adenosyl-L-homocysteine hydrolase," Collection of Czechoslovak Chemical Communications (1986), 51(2), pp. 459-477.

Ikeda et al., "AZD8848/DSP-3025, a novel potent TLR7 agonist antedrug, demonstrates efficacy against airway obstruction and other inflammatory endpoint in Guinea pig models of Rhinitis and asthma with acute and weekly dosing," ATS, New Orleans, May 2010.

Isobe et al., "Synthesis and structure-activity relationships of 2-substituted-8-hydroxyadenine derivatives as orally available interferon inducers without emetic side effects," Bioorganic & Medicinal Chemistry, 2003, 11(17), pp. 3641-3647.

Isobe, Y et al., "Synthesis and biological evaluation of novel 9-substituted-8-hydroxyadenine derivatives as potent interferon inducers," J. Med. Chem., 2006, 49 (6), pp. 2088-2095.

(56) References Cited

OTHER PUBLICATIONS

Itahara, "Control of liquid-crystalline properties by base pairing of adenine and thymine," ChemPhysChem, 2002, 3(4), pp. 378-379.
Korc "Pathways for aberrant angiogenesis in pancreatic cancer" Molecular Cancer 2(8):1-8 (2003).
Krueger et al. "Tilorone hydrochloride: an orally active antiviral agent" Science 169(3951):1213-1214 (1970).
Kurimoto et al., "Prodrugs of 9-benzyl-8-hydroxy-2-(2-hydroxyethylthio)adenine: potent interferon inducing agents in monkeys," Chemical & Pharmaceutical Bulletin, 2004, 52(4), pp. 466-469.
Kurimoto et al., "Synthesis and biological evaluation of 8-oxoadenine derivatives as Toll-like Receptor 7 agonists introducing the antedrug concept," J. Med. Chem., 2010, 53, pp. 2964-2972.
Kurimoto et al., "Synthesis and evaluation of 2-substituted 8-hydroxyadenines as potent interferon inducers with improved oral bioavailabilities," Bioorganic & Medicinal Chemistry, 2004, 12(5), pp. 1091-1099.
Kurimoto et al., "Synthesis and structure-activity relationships of 2-amino-8-hydroxyadenines as orally interferon nterferon inducing agents," Bioorganic & Medicinal Chemistry, 2003, 11(24), pp. 5501-5508.
Laino, Oncology Times(Jan. 25, 2008) vol. 30, Issue 2 p. 15.
Lee et al. "Activation of anti-hepatitis C virus responses via Toll-like receptor 7" Proc. Natl. Acad. Sci. USA 103(6): 1828-1833 (2006).
Lee et al."Molecular basis for the immunostimulatory activity of guanine nucleoside analogs: Activation on of Toll-like receptor 7" Proc. Natl. Acad. Sci. USA 100(11):6646-6651 (2003).
Matsui et al., "Mechanisms of inhibition of type-2 Cytokines by novel TLR7 agonist antedrugs," ATS New Orleans, May 2010.
Mayer et al. "Tilorone hydrochloride: mode of action" Science 169(951): 1214-1215 (1970).
McInally et al, "Identification of a novel TLR7 agonist antedrug," EFMC-ISMC 201, Brussels, Belgium, Sep. 5-9, 2010.
McInally, "Identification and pharmacology of novel TLR7 agonist antedrugs," RSC BMSC Inflammation meeting Nov. 18, 2010.
Mogulkoc et al. "Pulmonary function in idiopathic pulmonary fibrosis and referral for lung transplantation" Am J Respir Crit Care Med. 164(1):103-108 (2001).
Nichol et al. "Stimulation of murine interferon by a substituted pyrimidine" Antimicrobial Agents and Chemotherapy 9(3):433-439 (1976).
Palmer et al. "Highly drug-resistant HIV-1 clinical isolates are cross-resistant to many antiretroviral compounds in current clinical development" AIDS 13(6): 661-667 (1999).
Reiter et al. "Cytokine induction in mice by the immunomodulator imiquimod" Journal of Leukocyte Biology 55(2):234-240 (1994).
Spassova et al., "Synthesis of N-(3-Azido-2-hydroxypropyl), N-(3-Phthalimido-2-hydroxypropyl) and N-(3-Amino-2-hydroxypropyl) Derivatives of Heterocyclic Bases," Collection of Czechoslovak chemical Communications, 59(5), 1153-1174 (1994).
Stringfellow et al. "Antiviral and interferon-inducing properties of 1,5-diamino anthraquinones" . Antimicrobial Agents and Chemotherapy 15(1):111-118 (1979).
Tojo et al., "Synthesis and biological evaluation of a novel TLR7 agonist with an antedrug strategy," EFMC-ISMC 201, Brussels, Belgium, Sep. 5-9, 2010.
Zalutsky "Targeted radiotherapy of brain tumours" British Journal of Cancer 90(8):1469-1473 (2004).
Falco et al., "2,4-Diaminopyrimidines as antimalarials. i.1 5-aryloxyl and 5-alkoxyl derivatives," Journal of the American Chemical Society 73(8): 3753-3758 (1951).
Tarkoy et al., "Nucleic-acid analogues with constraint conformational flexibility in the sugar-phosphate backbone ("Bicyclo-DNA")," Helvetica Chimica Acta, 76(1): 481-510 (1993).
Yoshimoto et al., "Correlation analysis of Baker's studies on enzyme inhibition. 2. Chymotrypsin, trypsin, thymidine phosphorylase, uridine phosphorylase, thymidylate synthetase, cytosine nucleoside deaminase, dihydrofolate reductase, malate dehydrogenase, glutamate dehydrogenase, lactate dehydrogenase, and glyceraldehyde-phosphate dehydrogenase," Journal of Medicinal Chemistry, 19(1): 71-98 (1976).
Biffen et al. "Novel TLR7 agonists for the treatment of allergic diseases," Toll 2011 Meeting, Riva del Garda, Italy, May 4-7, 2011, Abstract.
Eiho et al. "Mechanism of long-lasting suppression against Th2 immune response in the lung by a novel antedrug TLR7 agonist," European Respiratory Society Annual Congress, Amsterdam, Sep. 24-28, 2011, Abstract and Poster.
Greiff et al. "Repeated intranasal TLR7 stimulation reduces allergen responsiveness in allergic rhinitis," European Respiratory Society Annual Congress, Amsterdam, Sep. 24-28, 2011, Abstract and Poster.
"Aerosols, Nasal Sprays, Metered-Dose Inhalers, and Dry Powder Inhalers", United States Pharmacopeia 29, general chapter 601 (2010).
"Preparations for Inhalation: Aerodynamic Assessment of Fine Particles", European Pharmacopeia, 5.8, Section 2.9.18, pp. 274-285 (2008).
Larran, J.M., "Micronisation of Pharmaceutical Powders for Use in Inhalation", Pharmaceutical Manufacturing and Packing Sourcer (Spring 2005).
Berge et al., "Pharmaceutical Salts", Journal of Pharmaceutical Sciences 66(1) (Jan. 1977).
Handbook of Pharmaceutical Salts, Eds. Stahl, Wermuth, Wiley-VCH (2002), pp. 90-96.
English translation of an Opposition against Ecuadorean Patent Application No. SP-2010-10265, which was filed Oct. 22, 2010.

* cited by examiner

PHARMACEUTICALLY ACCEPTABLE SALTS OF METHYL (3-{ [[3-(6-AMINO-2-BUTOXY-8-OXO-7,8-DIHYDRO-9H-PURIN-9-YL) PROPYL] (3-MORPHOLIN-4-YLPROPYL) AMINO] METHYL }PHENYL) ACETATE AND THEIR USE IN THERAPY

RELATED APPLICATIONS

The present application is a U.S. National Phase Application of International Application No. PCT/SE2008/051465, filed Dec. 16, 2008, which claims the benefit of U.S. Provisional Patent Application No. 61/014,164, filed Dec. 17, 2007, both of which are hereby incorporated by reference in their entirety.

NAMES OF PARTIES TO A JOINT RESEARCH AGREEMENT

The subject matter claimed in this application was made as a result of activities undertaken within the scope of a joint research agreement dated Dec. 19, 2003, between AstraZeneca AB and Sumitomo Pharmaceuticals Co., Ltd. All of the rights and obligations of Sumitomo Pharmaceuticals Co., Ltd. as defined in the joint research agreement between AstraZeneca AB and Sumitomo Pharmaceuticals Co., Ltd. were assumed by Dainippon Sumitomo Pharma Co., Ltd., a company created by the merger of Dainippon Pharmaceuticals Co., Ltd. and Sumitomo Pharmaceuticals Co., Ltd. effective Oct. 3, 2005.

The present invention relates to salts of an 8-oxoadenine derivative, pharmaceutical compositions containing them and their use in therapy.

Methyl (3-{[[3-(6-amino-2-butoxy-8-oxo-7,8-dihydro-9H-purin-9-yl)propyl](3-morpholin-4-ylpropyl)amino]methyl}phenyl)acetate is specifically disclosed in Example 2-37 of published International Patent Application No. WO 2005/092893 as an immuno-modulating compound that acts via Toll-like Receptor 7 (TLR7).

In the formulation of drug substances, it is important for the drug substance (active compound) to be in a form in which it can be conveniently handled and processed. This is of importance, not only from the point of view of obtaining a commercially-viable manufacturing process for the drug substance itself, but also from the point of view of subsequent manufacture of pharmaceutical formulations comprising the active compound and suitable excipients. In this connection, the chemical stability and the physical stability of the active compound are important factors. The active compound, and formulations containing it, must be capable of being effectively stored over appreciable periods of time, without exhibiting any significant change in the physico-chemical characteristics (e.g. chemical composition, density, hygroscopicity and solubility) of the active compound.

Furthermore, if the active compound is to be incorporated into a formulation for pulmonary administration, e.g., via a dry powder inhaler such as the Turbuhaler® device, it is desirable if the active compound can be readily micronised to yield a powder with good flow properties and comprising a high fine particle fraction (i.e. a fraction in which the active compound particles have a mass median diameter (MMD) of less than or equal to 10 μm (micrometer)). Such a fraction is capable of being carried deep into the lungs leading to faster and increased absorption of the active compound.

The person skilled in the art will appreciate that, typically, if a drug substance can be readily obtained in a stable form, such as a stable crystalline form, advantages may be provided, in terms of ease of handling, ease of preparation and extended shelf-life of suitable pharmaceutical formulations, and a more reliable solubility profile.

It has now surprisingly been found possible to prepare certain salts of methyl (3-{[[3-(6-amino-2-butoxy-8-oxo-7,8-dihydro-9H-purin-9-yl)propyl](3-morpholin-4-ylpropyl)amino]methyl}phenyl)acetate having improved physico-chemical properties compared to the free base compound, which are capable of being formulated in a dry powder formulation for pulmonary administration.

The structure of methyl (3-{[[3-(6-amino-2-butoxy-8-oxo-7,8-dihydro-9H-purin-9-yl)propyl](3-morpholin-4-ylpropyl)amino]methyl}phenyl)acetate is shown below:

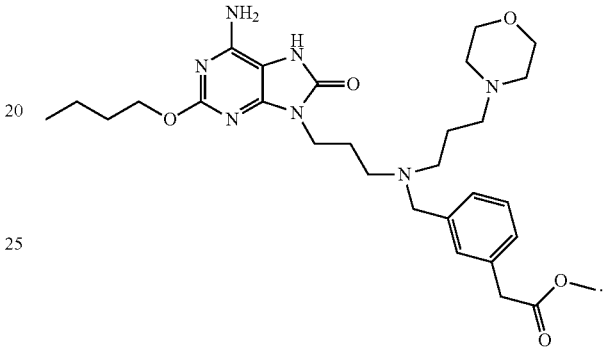

Thus, in accordance with the present invention, there is provided a hydrochloric acid, hydrobromic acid or maleic acid salt of methyl (3-{[[3-(6-amino-2-butoxy-8-oxo-7,8-dihydro-9H-purin-9-yl)propyl](3-morpholin-4-ylpropyl)amino]methyl}phenyl)acetate (hereinafter referred to as the "hydrochloride, hydrobromide or maleate salt").

In another aspect, the invention provides a hydrochloric acid, hydrobromic acid or maleic acid salt of methyl (3-{[[3-(6-amino-2-butoxy-8-oxo-7,8-dihydro-9H-purin-9-yl)propyl](3-morpholin-4-ylpropyl)amino]methyl}phenyl)acetate which exhibits the characteristic X-ray powder diffraction peaks (expressed in degrees 2θ) shown in Table A, B or C respectively (see Example 4 hereinafter).

The invention also provides solvates (including hydrates) of the hydrochloride, hydrobromide or maleate salt. However, the hydrochloride, hydrobromide or maleate salt is preferably anhydrous, and is preferably in non-solvated form.

In an embodiment of the invention, the hydrochloride, hydrobromide or maleate salt or solvate thereof has crystalline properties and is preferably at least 50% crystalline, more preferably at least 60% crystalline, still more preferably at least 70% crystalline and most preferably at least 80% crystalline. Crystallinity can be estimated by conventional X-ray diffractometry techniques.

In another embodiment of the invention, the hydrochloride, hydrobromide or maleate salt or solvate thereof is from 50%, 60%, 70%, 80% or 90% to 95%, 96%, 97%, 98%, 99% or 100% crystalline.

The preparation of methyl (3-{[[3-(6-amino-2-butoxy-8-oxo-7,8-dihydro-9H-purin-9-yl)propyl](3-morpholin-4-ylpropyl)amino]methyl}phenyl)acetate is described in published International Patent Application No. WO 2005/092893. The hydrochloride, hydrobromide and maleate salts (including solvated forms) of this compound can be prepared according to known techniques. However, it will be apparent to the person skilled in the art that there will be other possible routes for making this compound and its salts.

The salts (including the solvated forms) according to the invention are useful as modulators of TLR7 activity and thus may administered to a mammal, including man, for the treatment of the following conditions or diseases:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, parainfluenza; bacterial diseases such as tuberculosis and mycobacterium avium, leprosy; other infectious diseases, such as fungal diseases, chlamydia, candida, aspergillus, cryptococcal meningitis, pneumocystis carni, cryptosporidiosis, histoplasmosis, toxoplasmosis, trypanosome infection and leishmaniasis.

Thus, the present invention provides a hydrochloric acid, hydrobromic acid or maleic acid salt of methyl (3-{[[3-(6-amino-2-butoxy-8-oxo-7,8-dihydro-9H-purin-9-yl)propyl](3-morpholin-4-ylpropyl)amino]methyl}phenyl)acetate or a solvate of the salt, for use in therapy.

In a further aspect, the present invention provides the use of a hydrochloric acid, hydrobromic acid or maleic acid salt of methyl (3-{[[3-(6-amino-2-butoxy-8-oxo-7,8-dihydro-9H-purin-9-yl)propyl](3-morpholin-4-ylpropyl)amino]methyl}phenyl)acetate or a solvate of the salt, in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

In particular, the salts (including the solvated forms) according to the invention may be used in the treatment of asthma, COPD, allergic rhinitis, allergic conjunctivitis, atopic dermatitis, cancer, hepatitis B, hepatitis C, HIV, HPV, bacterial infections and dermatosis.

The invention therefore provides a method of treating an inflammatory disease in a patient suffering from, or at risk of, said disease, which comprises administering to the patient a therapeutically effective amount of a hydrochloric acid, hydrobromic acid or maleic acid salt of methyl (3-{[[3-(6-amino-2-butoxy-8-oxo-7,8-dihydro-9H-purin-9-yl)propyl](3-morpholin-4-ylpropyl)amino]methyl}phenyl)acetate or a solvate of the salt.

The invention also provides a method of treating an airways disease, e.g. a reversible obstructive airways disease such as asthma, in a patient suffering from, or at risk of, said disease, which comprises administering to the patient a therapeutically effective amount of a hydrochloric acid, hydrobromic acid or maleic acid salt of methyl (3-{[[3-(6-amino-2-butoxy-8-oxo-7,8-dihydro-9H-purin-9-yl)propyl](3-morpholin-4-ylpropyl)amino]methyl}phenyl)acetate or a solvate of the salt.

The invention still further provides a method of treating, or reducing the risk of, a disease or condition comprising or arising from abnormal cell growth (e.g. a cancer), which method comprises administering to a patient in need thereof a therapeutically effective amount of a hydrochloric acid, hydrobromic acid or maleic acid salt of methyl (3-{[[3-(6-amino-2-butoxy-8-oxo-7,8-dihydro-9H-purin-9-yl)propyl](3-morpholin-4-ylpropyl)amino]methyl}phenyl)acetate or a solvate of the salt.

For the above-mentioned therapeutic uses the dosage administered will, of course, vary with the salt employed, the mode of administration, the treatment desired and the disorder indicated. For example, the daily dosage of the (solvated) hydrochloride, hydrobromide or maleate salt, if inhaled, may be in the range from 0.05 micrograms per kilogram body weight (µg/kg) to 100 micrograms per kilogram body weight (µg/kg). Alternatively, if the (solvated) hydrochloride, hydrobromide or maleate salt is administered orally, then the daily dosage may be in the range from 0.01 micrograms per kilogram body weight (µg/kg) to 100 milligrams per kilogram body weight (mg/kg).

The hydrochloride, hydrobromide or maleate salt or solvate thereof according to the invention may be used on its own but will generally be administered in the form of a pharmaceutical composition in which the hydrochloride, hydrobromide or maleate salt or solvate thereof (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition may comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a hydrochloric acid, hydrobromic acid or maleic acid salt of methyl (3-{[[3-(6-amino-2-butoxy-8-oxo-7,8-dihydro-9H-purin-9-yl)propyl](3-morpholin-4-ylpropyl)amino]methyl}phenyl)acetate or a solvate of the salt in association with a pharmaceutically acceptable adjuvant, diluent or carrier.

The invention further provides a process for the preparation of a pharmaceutical composition of the invention which comprises mixing a hydrochloric acid, hydrobromic acid or maleic acid salt of methyl (3-{[[3-(6-amino-2-butoxy-8-oxo-7,8-dihydro-9H-purin-9-yl)propyl](3-morpholin-4-ylpropyl)amino]methyl}phenyl)acetate or a solvate of the salt with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

In an embodiment of the invention, the pharmaceutical composition is administered by inhalation (oral or nasal).

In a further embodiment, the pharmaceutical composition is administered by means of a dry powder inhaler (DPI).

The DPI may be "passive" or breath-actuated, or "active" where the powder is dispersed by some mechanism other than the patient's inhalation, for instance, an internal supply of compressed air. At present, three types of passive dry powder inhalers are available: single-dose, multiple unit dose or multidose (reservoir) inhalers. In single-dose devices, individual doses are provided, usually in gelatine capsules, and have to be loaded into the inhaler before use, examples of which include Spinhaler® (Aventis), Rotahaler® (GlaxoSmithKline), Aeroliser™ (Novartis), Inhalator® (Boehringer) and Eclipse (Aventis) devices. Multiple unit dose inhalers contain a number of individually packaged doses, either as multiple gelatine capsules or in blisters, examples of which include Diskhaler® (GlaxoSmithKline), Diskus® (GlaxoSmithKline) and Aerohaler® (Boehringer) devices. In multidose devices, drug is stored in a bulk powder reservoir from which individual doses are metered, examples of which include Turbuhaler® (AstraZeneca), Easyhaler® (Orion), Novolizer® (ASTA Medica), Clickhaler® (Innovata Biomed) and Pulvinal® (Chiesi) devices.

An inhalable pharmaceutical composition or dry powder formulation for use in a DPI can be prepared by mixing finely divided active ingredient (having a mass median diameter generally equal to or less than 10 µm, preferably equal to or less than 5 µm) with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. The powder mixture may then, as required, be dispensed into hard gelatine capsules, each containing the desired dose of the active ingredient.

Alternatively, an inhalable pharmaceutical composition may be prepared by processing a finely divided powder (e.g. consisting of finely divided active ingredient and finely divided carrier particles) into spheres that break up during the inhalation procedure. This spheronized powder is filled into the drug reservoir of a multidose inhaler, for example, that known as the Turbuhaler® in which a dosing unit meters the desired dose which is then inhaled by the patient.

Accordingly, the present invention also provides a dry powder inhaler, in particular a multiple unit dose dry powder inhaler, containing an inhalable pharmaceutical composition of the invention.

The hydrochloride, hydrobromide or maleate salt or solvate thereof according to the invention may also be administered in conjunction with other compounds used for the treatment of the above conditions.

The invention therefore further relates to combination therapies wherein a hydrochloride, hydrobromide or maleate salt or solvate thereof according to the invention, or a pharmaceutical composition comprising a hydrochloride, hydrobromide or maleate salt or solvate thereof according to the invention, is administered concurrently or sequentially or as a combined preparation with another therapeutic agent or agents, for the treatment of one or more of the conditions listed.

Figure 1:
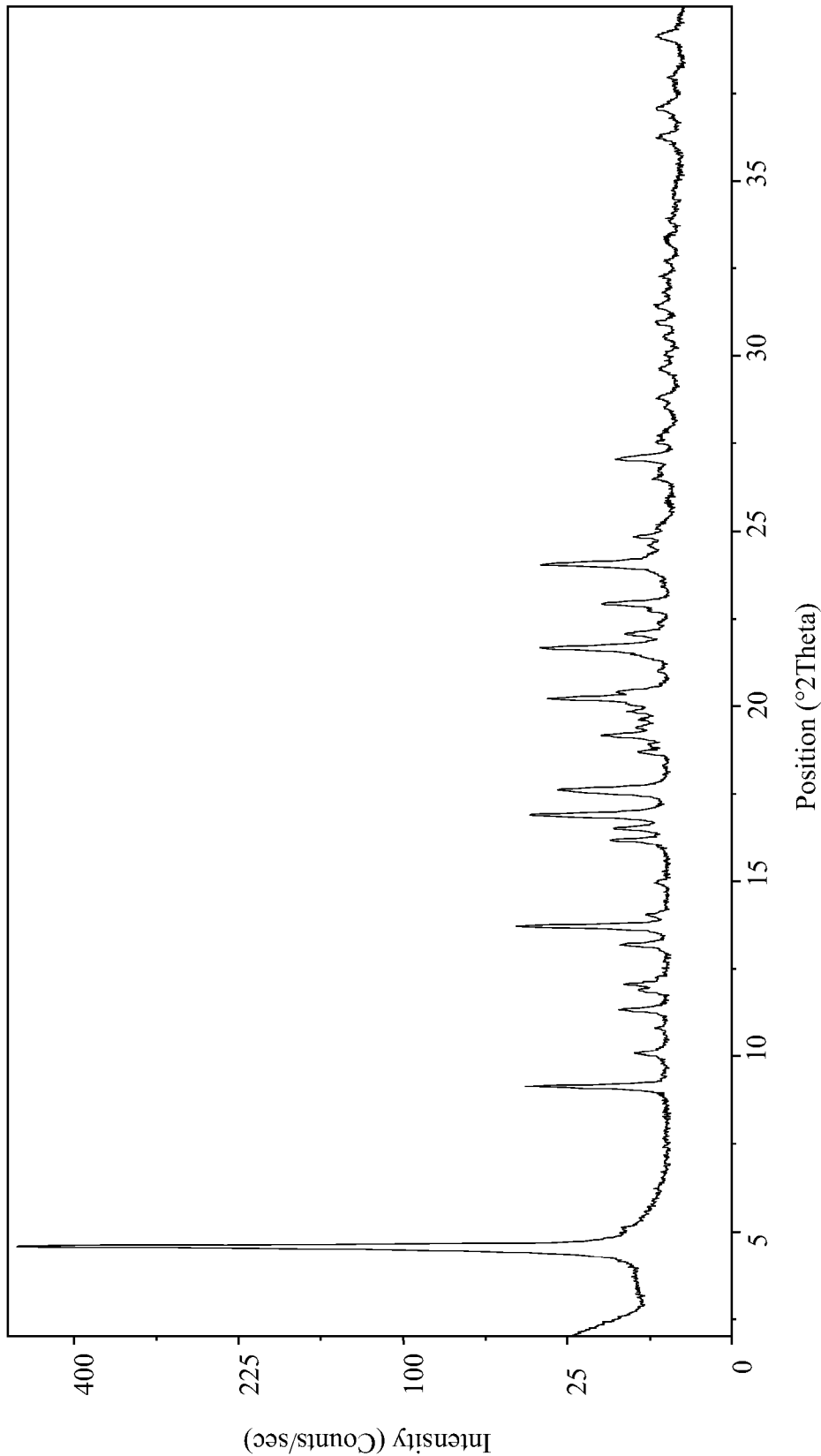
FIG. 1 shows an X-ray powder diffraction pattern of methyl (3-{[[3-(6-amino-2-butoxy-8-oxo-7,8-dihydro-9H-purin-9-yl)propyl](3-morpholin-4-ylpropyl)amino]methyl}phenyl)-acetate monohydrochloride.

The present invention will now be further explained by reference to the following illustrative examples.

General Methods $^1$H NMR spectra were recorded at 298K on a Varian Unity Inova 400 MHz (software: VNMR 6.1C and VNMRJ 1.1D; probe: Nalorac 5 mm DG400-5AT) or a Varian Mercury-VX 300 MHz (software: VNMR 6.1C; probe: Varian 5 mm AutoSW PFG) instrument. The central peaks of acetone-$d_6$ or dimethylsulphoxide (DMSO)-$d_6$ were used as internal references.

The following method was used for LC/MS analysis:
MS Instrument: Agilent 1100 series, equipped with APCI interface
LC instrument: Agilent 1100 series, equipped with UV-detector VWD, autosampler ALS, binary pump and degasser
LC-column: Chromolith® Speed ROD, RP-C18, ø 4.6×50 mm
Eluant: Solvent A: water+0.1% trifluoroacetic acid (TFA); Solvent B: acetonitrile+0.1% TFA
Conditions
    LC: flow 2.5 ml/minute; 5 to 95% B in gradient; run time 3.6 minutes; UV 220 nm
    MS: positive detection; capillary voltage 3 kV

EXAMPLE 1

Preparation of hydrochloric acid salt of methyl (3-{[[3-(6-amino-2-butoxy-8-oxo-7,8-dihydro-9H-purin-9-yl)propyl](3-morpholin-4-ylpropyl)amino] methyl}phenyl)acetate (1:1 salt)

(a) Methyl (3-{[[3-(6-amino-2-butoxy-8-oxo-7,8-dihydro-9H-purin-9-yl)propyl](3-morpholin-4-ylpropyl)amino] methyl}phenyl)acetate (40 mg, 0.07 mmol) was dissolved in ethyl acetate (5 mL) and 3.28M HCl/ethanol solution (21 µL, 0.07 mmol) was added. The solvent was removed by evaporation and the residue was dried in vacuo to give methyl (3-{[[3-(6-amino-2-butoxy-8-oxo-7,8-dihydro-9H-purin-9-yl)propyl](3-morpholin-4-ylpropyl)amino]methyl}phenyl) acetate monohydrochloride as the final product.

(b) A 80 mM solution of hydrochloric acid in methanol (65.0 µl, 5.2 µmol) was added to a solution of methyl (3-{[[3-(6-amino-2-butoxy-8-oxo-7,8-dihydro-9H-purin-9-yl)propyl](3-morpholin-4-ylpropyl)amino]methyl}phenyl)acetate (3.0 mg, 5.3 µmol) dissolved in methanol (1.5 ml) at room temperature. The solution was shaken at 60° C. for one hour, then cooled to 5° C. After 30 minutes, the solvent was left to slowly evaporate at 5° C., to give methyl (3-{[[3-(6-amino-2-butoxy-8-oxo-7,8-dihydro-9H-purin-9-yl)propyl](3-morpholin-4-ylpropyl)amino]methyl}phenyl)acetate monohydrochloride as the final product.

Further quantities of the monohydrochloride salt were prepared by the following method:

(c) A stoichiometric amount of a solution of hydrochloric acid in methanol (2.4 weight ratio, WR) was added to a suspension of methyl (3-{[[3-(6-amino-2-butoxy-8-oxo-7,8-dihydro-9H-purin-9-yl)propyl](3-morpholin-4-ylpropyl) amino]methyl}phenyl)acetate in methanol (4.0 WR) at 5° C. After stirring for 10 minutes, the white suspension had dissolved to give a clear solution. tert-Butyl methyl ether (5.1 WR) was added dropwise to the solution and following an addition of seed crystal of methyl (3-{[[3-(6-amino-2-butoxy-8-oxo-7,8-dihydro-9H-purin-9-yl)propyl](3-morpholin-4-ylpropyl)amino]methyl}-phenyl)acetate monohydrochloride prepared as described in (a) above, a white precipitate formed. After stirring for 5 minutes, tert-butyl methyl ether (11.2 WR) was added, and the suspension stirred for 1 hour at 5° C. The precipitate was filtered and washed with tert-butyl methyl ether (3.7 WR) to give methyl (3-{[[3-(6-amino-2-butoxy-8-oxo-7,8-dihydro-9H-purin-9-yl)propyl](3-morpholin-4-ylpropyl)amino]methyl}phenyl)acetate monohydrochloride as a solid (yield 90%).

Elemental Analysis

|  | Element | | | |
| --- | --- | --- | --- | --- |
|  | C | H | N | Cl |
| Found ratio (wt %) | 57.18 | 7.26 | 16.22 | 5.88 |
| Theoretical ratio (wt %) | 57.46 | 7.32 | 16.18 | 5.85 |

The stoichiometry, base to acid, of 1:1 was confirmed by NMR.

EXAMPLE 2

Preparation of hydrobromic acid salt of methyl (3-{[[3-(6-amino-2-butoxy-8-oxo-7,8-dihydro-9H-purin-9-yl)propyl](3-morpholin-4-ylpropyl)amino] methyl}phenyl)acetate (1:1 salt)

(a) A 1.55M solution of hydrobromide in ethanol (34 µl, 53 µmol) was added to a solution of methyl (3-{[[3-(6-amino-2-butoxy-8-oxo-7,8-dihydro-9H-purin-9-yl)propyl](3-morpholin-4-ylpropyl)amino]methyl}phenyl)acetate (30 mg, 0.053 mmol) in methanol (0.3 ml). The solution was dropped into tert-butyl methyl ether (0.9 ml) at room temperature. The clear solution was left at −10° C. for a week, after which time a crystalline substance precipitated. The crystalline material, methyl (3-{[[3-(6-amino-2-butoxy-8-oxo-7,8-dihydro-9H-purin-9-yl)propyl](3-morpholin-4-ylpropyl)amino] methyl}phenyl)acetate monohydrobromide, was filtered and dried.

Further quantities of the monohydrobromide salt were prepared by the following method:

(b) A stoichiotmetric amount of a solution of hydrobromic acid (aq., 48%) in methanol (0.8 WR) was added to a suspension of methyl (3-{[[3-(6-amino-2-butoxy-8-oxo-7,8-dihydro-9H-purin-9-yl)propyl](3-morpholin-4-ylpropyl)amino] methyl}phenyl)acetate in methanol (11.9 WR) at room temperature. After stirring for 10 minutes, the white suspension had dissolved to give a clear solution. A seed crystal of methyl (3-{[[3-(6-amino-2-butoxy-8-oxo-7,8-dihydro-9H-purin-9-yl)propyl](3-morpholin-4-ylpropyl)amino] methyl}phenyl)acetate monohydrobromide prepared as described in (a) above was added. tert-Butyl methyl ether (11.3 WR) was then added dropwise to the solution to give a white precipitate. The suspension was cooled to 3° C. and stirred for 1 hour. The precipitate was filtered and washed with tert-butyl methyl ether (3.7 WR) to give methyl (3-{[[3-(6-amino-2-butoxy-8-oxo-7,8-dihydro-9H-purin-9-yl)propyl](3-morpholin-4-ylpropyl)amino]methyl}phenyl)acetate monohydrobromide as a solid (yield 87.7–89.4%).

The stoichiometry, base to acid, of 1:1 was confirmed by NMR.

EXAMPLE 3

Preparation of maleic acid salt of methyl (3-{[[3-(6-amino-2-butoxy-8-oxo-7,8-dihydro-9H-purin-9-yl) propyl](3-morpholin-4-ylpropyl)amino] methyl}phenyl)acetate (1:2 salt)

(a) A 27 mM solution of maleic acid in 1,4-dioxane (0.5 ml, 13.5 µmol) was added to a solution of methyl (3-{[[3-(6- amino-2-butoxy-8-oxo-7,8-dihydro-9H-purin-9-yl)propyl](3-morpholin-4-ylpropyl)amino]methyl}phenyl)acetate (4 mg, 7 μmol) in 1,4-dioxane (0.75 ml) at room temperature and the mixture was left standing overnight. The next day, the solution was heated to 40° C. and shaken for one hour, and thereafter allowed to cool to room temperature. The solvent was evaporated at room temperature to give methyl (3-{[[3-(6-amino-2-butoxy-8-oxo-7,8-dihydro-9H-purin-9-yl)propyl](3-morpholin-4-ylpropyl)amino]methyl}phenyl)acetate dimaleate as the final product.

Further quantities of the dimaleate salt were prepared by the following method:

(b) Maleic acid (0.9 g, 7.8 mmol) was added to a mixture of methyl (3-{[[3-(6-amino-2-butoxy-8-oxo-7,8-dihydro-9H-purin-9-yl)propyl](3-morpholin-4-ylpropyl)amino]methyl}-phenyl)acetate (2.2 g, 3.9 mmol) in methanol (20 ml) and isopropyl alcohol (20 ml) and the mixture was heated to 50° C. until a clear solution was obtained. The solution was allowed to cool to room temperature and then seeded with a crystal of methyl (3-{[[3-(6-amino-2-butoxy-8-oxo-7,8-dihydro-9H-purin-9-yl)propyl](3-morpholin-4-ylpropyl)amino]methyl}-phenyl)acetate dimaleate prepared as described in (a) above. After 16 hours the solid was filtered and dried at 50° C. under high vacuum for 72 hours. Yield 2.96 g, 95%.

$^1$H NMR (DMSO-$d_6$); δ 9.88 (s, 1H), 7.32-7.22 (m, 4H), 6.43 (s, 2H), 6.11 (s, 4H), 4.12 (t, 2H), 3.95 (s, 2H), 3.71 (brs, 6H), 3.68 (s, 2H), 3.60 (s, 3H), 2.94-2.75 (m, 10H), 1.99-1.94 (m, 2H), 1.90-1.80 (m, 2H), 1.65-1.58 (m, 2H), 1.41-1.32 (m, 2H), 0.90 (t, 3H).

LC-MS m/z 570 APCI+ve

Elemental Analysis

|  | Element | | |
|---|---|---|---|
|  | C | H | N |
| Found ratio (wt %) | 55.8 | 6.2 | 12.1 |
| Theoretical ratio (wt %) | 55.4 | 6.4 | 12.2 |

The stoichiometry, base to acid, of 1:2 was confirmed by NMR.

EXAMPLE 4

X-Ray Powder Diffraction Analyses

General Procedures

X-ray powder diffraction (XRPD) analyses may be performed on samples prepared according to standard methods (see for example Giacovazzo et al., eds., Fundamentals of Crystallography, Oxford University Press (1992); Jenkins & Snyder, eds., Introduction to X-Ray Powder Diffractometry, John Wiley & Sons, New York (1996); Bunn, ed., Chemical Crystallography, Clarendon Press, London (1948); and Klug & Alexander eds., X-ray Diffraction Procedures, John Wiley & Sons, New York (1974)).

X-ray powder diffraction patterns of the salts described in Examples 1 to 3 above (in anhydrous form) were obtained as described below:

A Bragg-Brentano parafocusing powder X-ray diffractometer using monochromatic CuKα radiation (45 kV and 40 mA) was used for the analyses. The primary optics contained soller slits and an automatic divergence slit. Flat samples were prepared on zero background plates that were rotated during the meausurements. The secondary optics contained soller slits, an automatic anti scatter slit, a receiving slit and a monochromator. The diffracted signal was detected with a proportional xenon-filled detector. Diffraction patterns were collected between 2°≤2θ(theta)≤40° in a continous scan mode with a step size of 0.016° 2θ at a rate of 4° 2θ per minute. Raw data were stored electronically. Evaluation was performed on raw or smoothed diffraction patterns.

Figure 2:
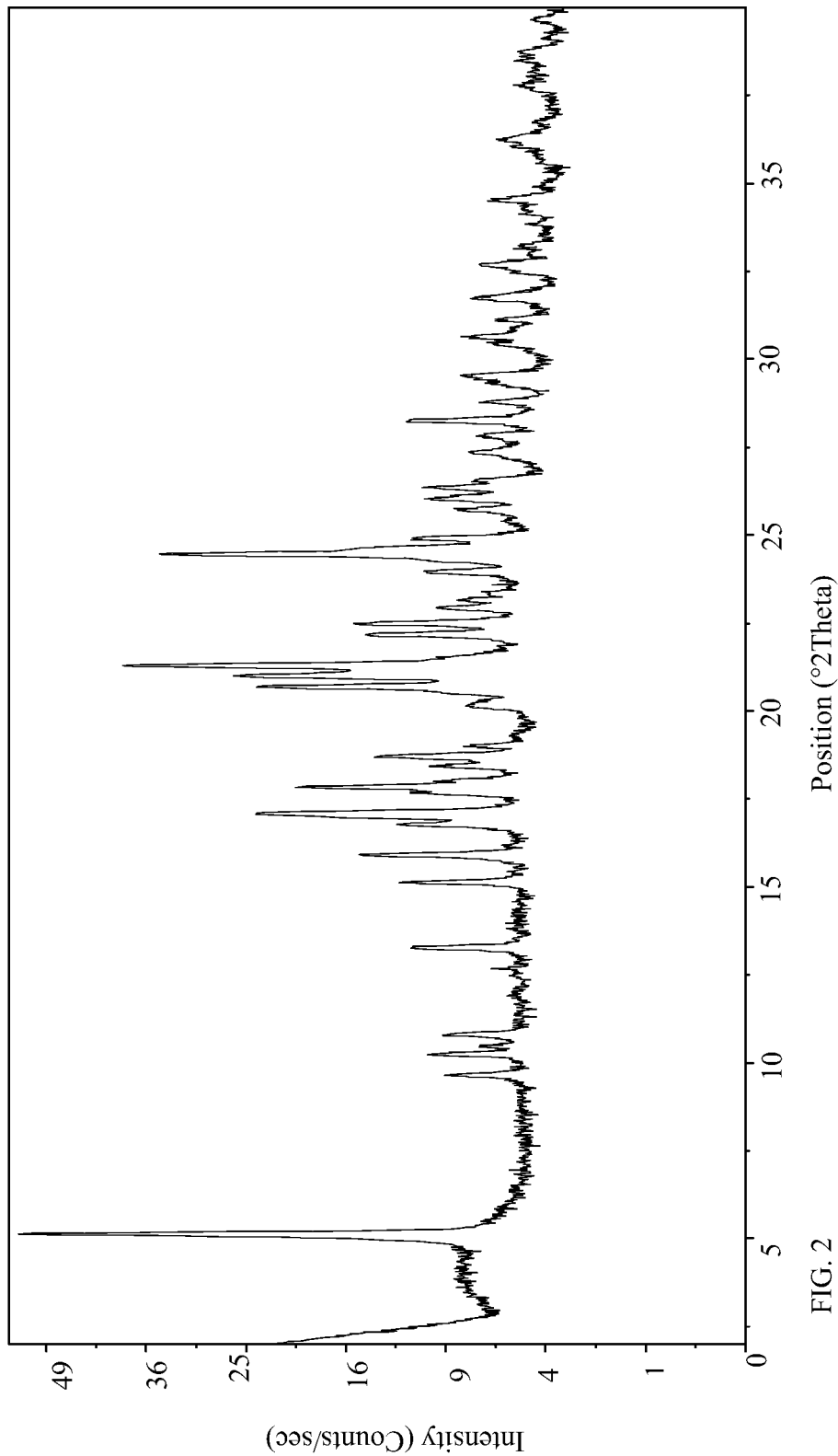
FIG. 2 shows an X-ray powder diffraction pattern of methyl (3-{[[3-(6-amino-2-butoxy-8-oxo-7,8-dihydro-9H-purin-9-yl)propyl](3-morpholin-4-ylpropyl)amino]methyl}phenyl)-acetate monohydrobromide.
Figure 3:
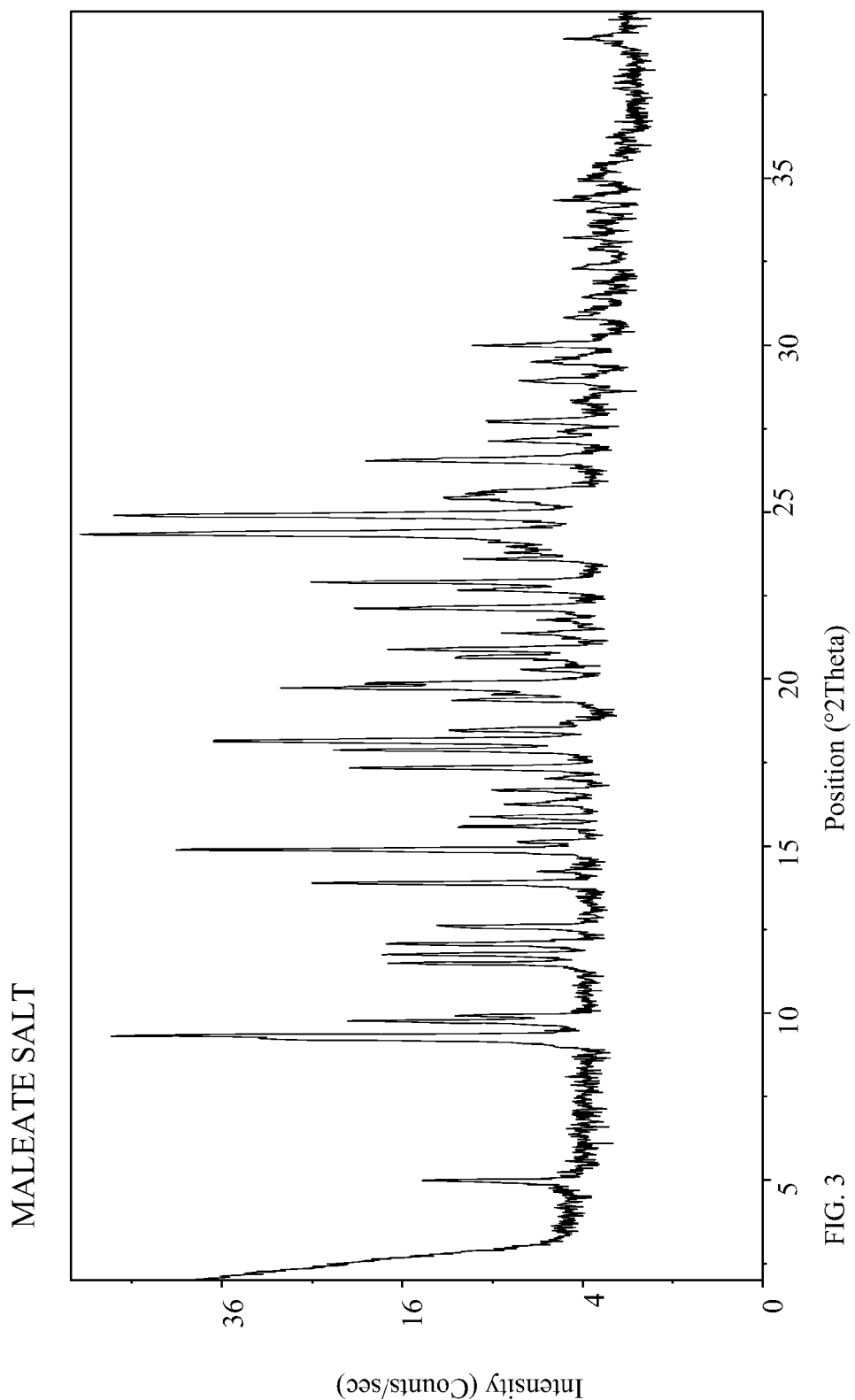
FIG. 3 shows an X-ray powder diffraction pattern of methyl (3-{[[3-(6-amino-2-butoxy-8-oxo-7,8-dihydro-9H-purin-9-yl)propyl](3-morpholin-4-ylpropyl)amino]methyl}phenyl)-acetate dimaleate.

A Panalytical X'pert PRO MPD θ-θ diffractometer in reflection mode was used for the above-mentioned measurements. A person skilled in the art can set up instrumental parameters for a powder X-ray diffractometer so that diffraction data comparable to the data presented can be collected. The results obtained are shown in FIG. 1, FIG. 2 and FIG. 3. Tables A, B and C below each list the 2θ (2 theta) values (Accuracy: +/−0.1° 2Ø), d-spacings and the relative intensities of the peaks shown in the X-ray diffraction patterns of respectively FIGS. 1, 2 and 3.

TABLE A

XRPD of Hydrochloride Salt

| 2Ø (°) | d-spacing (Å) | Relative Intensity (%) |
|---|---|---|
| 4.6 | 19.2 | 100 |
| 9.2 | 9.7 | 7 |
| 10.1 | 8.8 | 3 |
| 11.3 | 7.8 | 5 |
| 12.1 | 7.3 | 6 |
| 13.2 | 6.7 | 4 |
| 13.7 | 6.5 | 10 |
| 16.2 | 5.5 | 6 |
| 16.5 | 5.4 | 8 |
| 16.9 | 5.2 | 21 |
| 17.6 | 5.0 | 15 |
| 19.2 | 4.6 | 8 |
| 20.2 | 4.4 | 22 |
| 21.7 | 4.1 | 22 |
| 22.1 | 4.0 | 7 |
| 22.9 | 3.9 | 4 |
| 24.1 | 3.7 | 22 |
| 27.1 | 3.3 | 6 |

TABLE B

XRPD of Hydrobromide Salt

| 2Ø (°) | d-spacing (Å) | Relative Intensity (%) |
|---|---|---|
| 5.1 | 17.2 | 100 |
| 9.7 | 9.1 | 10 |
| 10.2 | 8.6 | 16 |
| 10.5 | 8.4 | 6 |
| 10.8 | 8.2 | 12 |
| 13.3 | 6.7 | 16 |
| 15.1 | 5.9 | 19 |
| 15.9 | 5.6 | 25 |
| 16.8 | 5.3 | 14 |
| 17.1 | 5.2 | 52 |
| 17.7 | 5.0 | 16 |
| 17.9 | 5.0 | 36 |
| 18.0 | 4.9 | 15 |
| 18.4 | 4.8 | 13 |
| 18.7 | 4.7 | 22 |
| 20.7 | 4.3 | 45 |
| 21.0 | 4.2 | 52 |
| 21.3 | 4.2 | 73 |
| 22.2 | 4.0 | 21 |
| 22.5 | 4.0 | 26 |
| 22.9 | 3.9 | 10 |
| 23.2 | 3.8 | 10 |
| 24.0 | 3.7 | 13 |
| 24.5 | 3.6 | 56 |

TABLE B-continued

XRPD of Hydrobromide Salt

| 2Ø (°) | d-spacing (Å) | Relative Intensity (%) |
|---|---|---|
| 24.9 | 3.6 | 14 |
| 25.7 | 3.5 | 14 |
| 26.1 | 3.4 | 16 |
| 26.3 | 3.4 | 13 |
| 27.3 | 3.3 | 9 |

TABLE C

XRPD of Maleate Salt

| 2Ø (°) | d-spacing (Å) | Relative Intensity (%) |
|---|---|---|
| 5.0 | 17.7 | 19 |
| 9.3 | 9.5 | 86 |
| 9.8 | 9.1 | 33 |
| 9.9 | 8.9 | 15 |
| 11.5 | 7.7 | 24 |
| 11.8 | 7.5 | 27 |
| 12.1 | 7.3 | 26 |
| 12.6 | 7.0 | 17 |
| 13.9 | 6.4 | 40 |
| 14.9 | 5.9 | 73 |
| 15.6 | 5.7 | 15 |
| 15.9 | 5.6 | 12 |
| 16.3 | 5.4 | 13 |
| 16.7 | 5.3 | 16 |
| 17.3 | 5.1 | 32 |
| 17.9 | 5.0 | 32 |
| 18.1 | 4.9 | 62 |
| 18.5 | 4.8 | 16 |
| 19.4 | 4.6 | 15 |
| 19.7 | 4.5 | 48 |
| 19.9 | 4.5 | 30 |
| 20.7 | 4.3 | 16 |
| 20.9 | 4.3 | 26 |
| 22.1 | 4.0 | 32 |
| 22.7 | 3.9 | 16 |
| 22.9 | 3.9 | 39 |
| 24.3 | 3.7 | 100 |
| 24.9 | 3.6 | 88 |
| 26.5 | 3.4 | 30 |

EXAMPLE 5

Differential Scanning Calorimetry (DSC)

Using standard methods, for example those described in Höhne, G. W. H. et al (1996), Differential Scanning calorimetry, Springer, Berlin, the calorimetric response of a test sample to increasing temperature was investigated using a TA Instruments Q1000 Modulated Temperature Differential Scanning calorimeter (MTDSC) using a modulation of ±0.50° C. in intervals of 40 seconds and a ramp rate of 5° C. per minute. Approximately 1 to 5 mg of test sample was placed in aluminium cups with lids (no crimping) under a nitrogen atmosphere.

It is well known that the DSC onset and peak temperatures may vary due to the purity of the sample and instrumental parameters, especially the temperature scan rate. A person skilled in the art can use routine optimization/calibration to set up instrumental parameters for a differential scanning calorimeter so that data comparable to the data presented here can be collected.

The melting temperature for a typical sample of the anhydrous monohydrochloride salt obtained in Example 1(c) was found to be 144° C.±3° C. (onset).

The melting temperature for a typical sample of the anhydrous monohydrobromide salt obtained in Example 2(b) was found to be 150° C.±3° C. (onset).

The melting temperature for a typical sample of the anhydrous dimaleate salt obtained in Example 3(b) was found to be 150° C.±3° C. (onset).

EXAMPLE 6

Particle Size Reduction

Particle size reduction using a 2" Spiral Jet Mill (SJM) was carried out on the following three test substances: the monohydrochloride salt according to Example 1 (invention salt), the dimaleate salt according to Example 3 (invention salt) and the free base compound, methyl (3-{[[3-(6-amino-2-butoxy-8-oxo-7,8-dihydro-9H-purin-9-yl)propyl](3-morpholin-4-ylpropyl)amino]methyl}phenyl)acetate (comparison compound).

A sieved batch of test substance was fed into the jet mill chamber, via a venturi feed system, by a vibratory feeder. Micronisation was achieved by particle collisions brought about by compressed gas (nitrogen) forced through angled nozzles in the jet mill chamber. Particles of different sizes develop different speeds and momentum and as the particle size is reduced the particles spiral towards the centre of the jet mill and exit via an exhaust into a collection bin. The process parameters that control the particle size, in addition to the inherent properties of the compound to be micronised, are the feed rate, grinding pressure and venturi pressure and these are summarised in Table I following.

TABLE I

| Test Substance | Amount processed (g) | Yield (%) | Feed rate | Venturi Pressure (bar) | Grind Pressure (bar) |
|---|---|---|---|---|---|
| Comparison compound | 1.7 | 1.7 | Constant flow | 5 (4) | 2 (1) |
| Dimaleate salt | 2.0 | 48 | Constant flow | 5 | 2 |
| Monohydrochloride salt | 37 | 85 | Constant flow | 5 | 1 |

Due to build-up of the comparison compound in the exhaust, the mill became plugged. Lowering of the grind/venturi pressures from ⅖ bar to ¼ bar had no significant beneficial effect in this respect. Thus, particle size reduction of the comparison compound was aborted after only 1.7 g of the intended 7 g had been loaded.

By contrast, the monohydrochloride and dimaleate salts were readily micronised and there was no significant build-up or blocking of the mill during processing.

EXAMPLE 7

Measurement of Fine Particle Fraction (FPF)

Procedure

Measurement of FPF, starting from substance as received, was carried out according to the following series of steps:
1. Particle size reduction (micronisation) of received substance.
2. Particle size measurement (after size reduction) using laser diffraction instrument.
3. Manual sample loading.
4. Deaggregation of powder and collection of aerosol in cascade impactor.

5. Quantification using high pressure liquid chromatography (HPLC) and calculation of FPF.

Three substances were tested: the monohydrochloride salt according to Example 1 (invention salt), the monohydrobromide salt according to Example 2 (invention salt) and the free base compound, methyl (3-{[[3-(6-amino-2-butoxy-8-oxo-7,8-dihydro-9H-purin-9-yl)propyl](3-morpholin-4-ylpropyl)amino]methyl}phenyl)acetate (comparison compound).

Particle Size Reduction

Particle size reduction (micronisation) was performed in a jet mill in which pressurised gas was used to make the substance particles collide at high speed in order to effect particle size reduction.

Particle Size Measurement

Particle size measurements were performed with laser diffraction using a Malvern Scirocco instrument. The results obtained are presented in Table 1 following.

TABLE 1

| Test substance | Pressure (bar) | d(0.1) (μm) | d(0.5) (μm) | d(0.9) (μm) |
| --- | --- | --- | --- | --- |
| Comparison compound | 4 | 0.6 | 1.7 | 4.1 |
| Monohydrochloride (invention) | 1.5 | 0.9 | 1.8 | 3.5 |
| Monohydrobromide (invention) | 1.5 | 0.8 | 1.9 | 4.1 |

Sample Loading

Doses of 1-2 mg were weighed manually (without scraping) into the cavities of a prototype inhaler (see below). Two experiments were run for each test substance and two doses were used in each experiment and, thus, in total, four doses of each test substance were used in the experiments. The samples were dried in nitrogen gas atmosphere overnight before conducting the experiments.

Experimental Set-Up and Deaggregation of Powder

The Next Generation Impactor, NGI, was used for the fine particle assessment. This cascade impactor is described in pharmacopoeias such as USP (general chapter <601> AEROSOLS, NASAL SPRAYS, METERED-DOSE INHALERS, AND DRY POWDER INHALERS, apparatus 5) and Eur. Pharmacopoeia (5.8 section 2.9.18 PREPARATIONS FOR INHALATION: AERODYNAMIC ASSESSMENT OF FINE PARTICLES, apparatus E), where there is a detailed description about how to set up, operate and calibrate the impactor for use at different flow rates. Two NGI impactors were used, one per experiment.

A simple prototype inhaler was used for the tests, consisting of an L-shaped cylindrical channel, comprising a vertical component and a horizontal component. The prototype inhaler was fitted via an USP-inlet to the NGI impactor. The micronised powder was transferred through the vertical channel into the bend of the prototype inhaler, (i.e. the bend of the L-shaped channel).

Each dose of 1-2 mg of powder was drawn with an airflow of 60 liters/min for 2 seconds (measured at the entrance of the induction port), entraining the powder located in the bend, and the aerosol thereafter moved through the horizontal component of the channel, through a spiral mouthpiece and into the NGI impactor. The drug powders were collected in the induction port and in eight cups (see references given above).

The withdrawal and collection of the drug powders was performed in an isolator (glove) box with a relative humidity level below 2%.

HPLC Analysis

The drug powder contents of the induction port and in the eight cups were then quantified using High Pressure Liquid Chromatography methodology as described in Table 2.

TABLE 2

| | Test substance | | |
| --- | --- | --- | --- |
| Parameter | Comparison cpd. | Monohydrochloride | Monohydrobromide |
| Column | Thermo Electron Hypersil Gold 50 mm × 3 mm. 3 μm particles | Symmetry C18 150 mm × 3 mm. 3.5 μm particles | Symmetry C18 150 mm × 3 mm. 3.5 μm particles |
| Column temperature (° C.) | 60 | 20 | 40 |
| Flow (ml/min) | 1.0 | 0.64 | 0.64 |
| Mobile phase A | 0.1% ammonium acetate in water | 0.02% trifluoroacetic acid in water | 0.02% trifluoroacetic acid in water |
| Mobile phase B | 0.1% ammonium acetate in water/acetonitrile (10/90%) | 0.02% trifluoroacetic acid in acetonitrile | 0.02% trifluoroacetic acid in acetonitrile |
| Composition | Isocratic, A/B: 60/40% | Isocratic, A/B: 81/19% | Isocratic, A/B: 81/19% |
| Injection volume (μl) | 20.0 | 75 | 75 |
| Detector wavelength (nm) | 283 | 244 | 244 |

Calculation

Key data used for the calculations of FPF as obtained from the HPLC analyses are presented in Table 3. The FPF's, as defined in the pharmacopoeia references above, were calculated.

TABLE 3

| Data | Test substance | | | | | |
|---|---|---|---|---|---|---|
| | Comparison cpd. | | Mono-hydro-chloride | | Mono-hydro-bromide | |
| | NGI1 | NGI2 | NGI1 | NGI2 | NGI1 | NGI2 |
| Delivered amount (μg) | 720 | 1396 | 1257 | 992 | 1123 | 975 |
| Collected in stage 3-8 (<4.5 μm) (μg) | 131 | 178 | 383 | 392 | 319 | 414 |
| Amount particles < 5 μm, extrapolated (μg) | 139 | 189 | 393 | 402 | 332 | 427 |
| FPF (% < 5 μm/delivered dose) | 19.3 | 13.6 | 31.3 | 40.6 | 29.6 | 43.8 |
| FPF (% < 5 μm/delivered dose), Average over NGI's | 16.4 | | 35.9 | | 36.7 | |

The invention claimed is:

1. Methyl (3-{[[3-(6-amino-2-butoxy-8-oxo-7,8-dihydro-9H-purin-9-yl)propyl](3-morpholin-4-ylpropyl)amino]methyl}phenyl)acetate monohydrochloride, characterized in that said compound has an X-Ray powder diffraction pattern with peaks at 2θ=4.6°+/−0.1°, 9.2°+/−0.1°, 12.1°+/−0.1° and 13.7°+/−0.1° when measured using CuKα radiation.

2. A compound as claimed in claim 1 which is at least 70% crystalline.

3. A pharmaceutical composition comprising a compound as claimed in claim 1, in association with a pharmaceutically acceptable adjuvant, diluent or carrier.

4. A pharmaceutical composition as claimed in claim 3 which is in the form of a dry powder formulation for use in inhalation therapy.

5. A dry powder inhaler containing a pharmaceutical composition as claimed in claim 4.

6. Methyl (3-{[[3-(6-amino-2-butoxy-8-oxo-7,8-dihydro-9H-purin-9-yl)propyl](3-morpholin-4-ylpropyl)amino]methyl}phenyl)acetate monohydrochloride, characterized in that said compound has an X-Ray powder diffraction pattern with peaks at 2θ=4.6°, 9.2°, 12.1° and 13.7° when measured using CuKα radiation.

7. Methyl (3-{[[3-(6-amino-2-butoxy-8-oxo-7,8-dihydro-9H-purin-9-yl)propyl](3-morpholin-4-ylpropyl)amino]methyl}phenyl)acetate monohydrochloride, characterized in that said compound has an X-Ray powder diffraction pattern with specific peaks at 2θ=4.6°+/−0.1°, 9.2°+/−0.1°, 12.1°+/−0.1°, 13.7°+/−0.1°, 16.5°+/−0.1°, 16.9°+/−0.1°, 17.6°+/−0.1° and 20.2°+/−0.1°, when measured using CuKα radiation.

* * * * *

UNITED STATES PATENT AND TRADEMARK OFFICE
CERTIFICATE OF CORRECTION

PATENT NO. : 8,673,907 B2  Page 1 of 1
APPLICATION NO. : 12/808627
DATED : March 18, 2014
INVENTOR(S) : McInally et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 387 days.

Signed and Sealed this
Twenty-ninth Day of September, 2015

Michelle K. Lee
*Director of the United States Patent and Trademark Office*